United States Patent
Obata et al.

(10) Patent No.: US 10,668,157 B2
(45) Date of Patent: Jun. 2, 2020

(54) ANIONIC DRUG-CONTAINING MEDICAL DEVICE

(71) Applicants: SEED CO., LTD., Tokyo (JP); SENJU PHARMACEUTICAL CO., LTD., Osaka-shi, Osaka (JP)

(72) Inventors: Haruka Obata, Tokyo (JP); Kiyoshi Shoji, Tokyo (JP); Yoshiko Yamazaki, Tokyo (JP); Toru Matsunaga, Tokyo (JP); Takao Sato, Tokyo (JP); Wakiko Asayama, Kobe (JP); Shinichi Yasueda, Kobe (JP)

(73) Assignees: SEED CO., LTD., Tokyo (JP); SENJU PHARMACEUTICAL CO., LTD., Osaka-Shi (JP)

( * ) Notice: Subject to any disclaimer, the term of this patent is extended or adjusted under 35 U.S.C. 154(b) by 0 days.

(21) Appl. No.: 15/304,409

(22) PCT Filed: Apr. 16, 2015

(86) PCT No.: PCT/JP2015/061670
§ 371 (c)(1),
(2) Date: Oct. 14, 2016

(87) PCT Pub. No.: WO2015/159942
PCT Pub. Date: Oct. 22, 2015

(65) Prior Publication Data
US 2017/0043017 A1 Feb. 16, 2017

(30) Foreign Application Priority Data

Apr. 17, 2014 (JP) ................... 2014-085664

(51) Int. Cl.
| A61K 9/14 | (2006.01) |
|---|---|
| A61K 9/00 | (2006.01) |
| A61K 47/32 | (2006.01) |
| A61K 9/06 | (2006.01) |
| A61K 31/352 | (2006.01) |
| A61K 31/661 | (2006.01) |
| A61K 47/00 | (2006.01) |

(52) U.S. Cl.
CPC ............. *A61K 47/32* (2013.01); *A61K 9/06* (2013.01); *A61K 31/352* (2013.01); *A61K 31/661* (2013.01)

(58) Field of Classification Search
None
See application file for complete search history.

(56) References Cited

U.S. PATENT DOCUMENTS

| 6,277,366 B1 | 8/2001 | Goto et al. | |
|---|---|---|---|
| 7,811,601 B2 | 10/2010 | Sato et al. | |
| 2008/0193497 A1 | 8/2008 | Samuelsen et al. | |
| 2011/0306661 A1* | 12/2011 | Sato ................. | G02B 1/043 514/456 |

FOREIGN PATENT DOCUMENTS

| CN | 101129342 | * | 2/2008 |
|---|---|---|---|
| CN | 103059219 A | | 4/2013 |
| EP | 537774 | * | 4/1993 |
| EP | 0 595 226 | * | 5/1994 |
| JP | 63-270510 A | | 11/1988 |
| JP | 6-145456 A | | 5/1994 |
| JP | 11-228449 A | | 8/1999 |
| JP | 2004-307574 A | | 11/2004 |
| RU | 2175561 C2 | | 11/2001 |
| WO | WO 96/38174 A1 | | 12/1996 |
| WO | WO 2010/109043 A1 | | 9/2010 |

OTHER PUBLICATIONS

Parra et al., Biomacromolecules, 2009, 10(11), 3055-3061.*
Journal of Membrane Science (2014), 451, 205-215.*
Extended European Search Report issued in European Application No. 15780612.6 dated Oct. 25, 2017.
Parra-Ruiz et al., "Polymeric systems containing dual biologically active ions," European Journal of Medicinal Chemistry, vol. 46, 2011 (available online Aug. 23, 2011), pp. 4980-4991.
Solovskii et al., "Benzyl- and phenoxymethylpenicillin salts based on aminoalkyl methacrylate polymers", CAPLUS Database, 1977, 3 pages, Abstract only.
Solovskii et al., Khimiko-Farmatsevticheskii Zhurnal, Izdatel'stvo Folium, RU, vol. 11, No. 3, XP009500728, Jan. 1, 1977, 4 pages.
Chinese Office Action with the English translation issued in corresponding Chinese Application No. 201580019988.9 dated Oct. 23, 2018.
Japanese Notice of Reasons for Refusal with the English translation issued in corresponding Japanese Application No. 2016-513826 dated Nov. 6, 2018.
International Search Report (form PCT/ISA/210), dated Jul. 21, 2015, for International Application No. PCT/JP2015/061670, with an English translation.

(Continued)

*Primary Examiner* — Shobha Kantamneni
(74) *Attorney, Agent, or Firm* — Birch, Stewart, Kolasch & Birch, LLP (57) ABSTRACT

The purpose of the present invention is to provide a polymer gel that can increase drug content ratio and reduce undesirable influence on gel strength and shape stability after the drug release, compared with the conventional techniques. The purpose can be achieved by an anionic drug-containing medical device comprising: (1) an anionic drug; and (2) a copolymer which contains, as constituents, a cationic monomer comprising a condensation product of an alkyl quaternary ammonium compound having a substituted or unsubstituted aralkyl group and (meth)acrylic acid or a salt of the condensation product and a monomer capable of copolymerizing with the condensation product or the salt of the condensation product.

4 Claims, 2 Drawing Sheets

(56) References Cited

OTHER PUBLICATIONS

Russian Office Action and Search Report, dated Oct. 18, 2018, for Russian Application No. 2016144681, with English translations.
European Office Action, dated Aug. 16, 2019, for European Application No. 15780612.6.

* cited by examiner

ANIONIC DRUG-CONTAINING MEDICAL DEVICE

CROSS REFERENCE TO RELATED APPLICATIONS

This application claims the benefit of priority of Japanese Patent Application No. 2014-085664, filed on Apr. 17, 2014, which is incorporated by reference herein in its entirety.

TECHNICAL FIELD

The present invention relates to an anionic drug-containing medical device.

BACKGROUND ART

Intravitreal injections, insertions of punctal plugs, drug administrations are known among others as therapeutic techniques for ocular disorders such as glaucoma and dry eyes. However, intravitreal injections and insertions of punctal plugs are therapies that are invasive to eyes and hence they are accompanied by problems such as those of giving pain, giving foreign body sensation and so on to patients. Drug Administrations of drugs, on the other hand, can give rise to a problem of not achieving the intended effects depending on the dose and the method of administration selected for the patient. Various attempts have been made to find means of drug administration that provide remarkable therapeutic effects.

When administering a drug by instillation, the drug that is added to the ophthalmic solution to be administered and dropped into an eye is rapidly diluted with tears and discharged by lacrimal passage. Thus, in order to keep the concentration of the drug to an effective level, a large dose to be added to the ophthalmic solution and/or the ophthalmic solution to be administered frequently is needed. Both consequently give a heavy burden on patients.

Additionally, administration of a drug to a contact lens wearer by instillation can entail adverse effects such as shape distortion and/or quality degradation of the contact lens.

Furthermore, some antiseptic that is normally contained in commercially available ophthalmic drugs has a risk for developing allergies by absorption into the contact lens. Therefore, medicinal therapies involving the use of instillation are not suited to contact lens wearers.

In view of the above identified circumstances, techniques using a drug delivery system (DDS) that delivers a drug to the ocular tissues of the eyes of a patient by wearing lenses that are made to contain a therapeutic drug in advance, or drug-containing contact lenses, have been disclosed for the purpose of treating patients who wear contact lenses in a safe, simple and easy manner.

Known polymer gels that are applicable to therapeutic drug-containing contact lenses include those having a quaternary ammonium salt at a side chain thereof so as to have it adsorb and hold an anionic drug (see Patent Literature 1 listed below, which is incorporated by reference herein in its entirety) and those made to show a lopsided molar ratio between the anionic monomer and the cationic monomer thereof, which are components of the hydrogel, so as to cause the excess cationic monomers to be bonded to an anionic drug by ionic bonding (see Patent Literature 2 listed below, which is incorporated by reference herein in its entirety)

PRIOR ART LITERATURES

Patent Literatures

[Patent Literature 1] Japanese Patent Application Laid-Open Publication No. 06-145456
[Patent Literature 2] Japanese Patent Application Laid-Open Publication No. 2004-307574

DISCLOSURE OF THE INVENTION

Problem to be Solved by the Invention

Polymer gels described in Patent Literatures 1 and 2 are formed by compounding a cationic monomer having a cationic group, which cationic monomer is brought in as a component of the polymer gel base material, with other components and causing a selected anionic therapeutic drug to be bonded to the cationic group by ionic bonding. Either one of such polymer gels as described in the patent literatures is required to contain the cationic monomer used by a large amount in order to accommodate the large amount of the therapeutic drug to be contained in the inside of the gel.

However, cationic monomers generally have a high moisture holding capacity and therefore, as the compounding ratio of the cationic monomer contained in a polymer gel is raised, the moisture holding ratio of the polymer gel that is obtained as final product inevitably rises. On the other hand, the strength of the polymer gel falls as the moisture holding ratio thereof rises. Thus, as the drug content is raised in a polymer gel by increasing the compounding ratio of cationic monomer, there arises a problem that the strength of the obtained polymer gel inevitably falls as a result of the increase in the moisture holding ratio thereof. With regard to this problem, for instance, Patent Literature 1 describes in paragraph [0015] thereof that the cationic monomer can be added only by 5 mol % at most relative to the total quantity of the monomers that form the polymer gel and that the mechanical strength of the obtained polymer gel will fall if the cationic monomer is added above that level.

Additionally, as a drug-containing polymer gel releases the drug it contains, the shape of the polymer gel can easily become distorted to an undesirable extent. For instance, with the composition of a polymer gel described in Patent Literature 1, the polymer gel keeps showing a desirable shape before it releases the drug because of an interaction between the polymer gel and the drug but, after releasing the drug, the shape of the polymer gel is degraded to an undesirable extent because the interaction becomes no longer existent. The shape degradation after the release of the drug contained is particularly remarkable when the compounding ratio of cationic monomers is high.

A polymer gel described in Patent Literature 2 contains an anionic monomer in addition to the cationic monomer as its component. A polymer gel as described in Patent Literature 2 does not show any remarkable shape degradation after the polymer gel releases the drug contained in it because the anionic monomer and the cationic monomer are bonded to each other in it due to an electrostatic interaction between them and the compounding ratio between the anionic monomer and the cationic monomer is not remarkably lopsided. However, the compounding ratio of the anionic monomer and the cationic monomer is subjected to a certain limit because when they are made to show a remarkably lopsided ratio in order to allow the polymer gel to be able to contain the drug to a high content ratio, there arises a risk that the shape of the polymer gel is considerably degraded after the release of the drug contained. Thus, a polymer gel described in Patent Literature 2 is accompanied by a problem that the content ratio of the drug it contains is limited.

As described above, polymer gels described in Patent Literatures 1 and 2 are subjected to limitations in terms of the content ratio of the drugs they respectively contain. In other words, with each of Patent Literatures, if the content ratio of the drug contained in a polymer gel described in it is raised, there can arise a problem of a fall of the gel strength and degraded shape stability once the drug contained is released.

In view of the above identified problems of the prior art, therefore, the problem to be solved by the present invention is to provide a polymer gel that can increase the drug content ratio and reduce the undesirable influence on gel strength and shape stability after the drug release, compared with polymer gels described in Patent Literatures 1 and 2, and also to provide a drug-containing medical device applying the polymer gel.

Means for Solving the Problem

The inventors of the present invention made intensive research efforts for the purpose of solving the above identified problems of the prior art and closely looked into the relationship between the structure of the cationic monomer to be used for forming a polymer gel and the moisture holding property and the shape stability of the polymer gel formed by using the cationic monomer. As a result, the inventors came to pay attention to a condensation product of an alkyl quaternary ammonium compound having an aralkyl group and (meth)acrylic acid.

When the condensation product is employed as a component of a polymer gel base material, it can be expected to suppress the rise of the moisture holding ratio of the polymer gel to be obtained even when the condensation product is compounded in the polymer gel base material at a high compounding ratio because of the hydrophobic effect of the benzene ring in the molecule thereof. Thus, the inventors of the present invention prepared an anionic drug-containing gel, using the condensation product as cationic monomer, and succeeded in suppressing the above identified problems of polymer gels described in Patent Literatures 1 and 2 including the rise of the moisture holding ratio of the polymer gel base material due to an increase of the cationic monomer compounding ratio and the fall of the strength of the base material probably attributable to the rise of the moisture holding ratio. Furthermore, the inventors of the present invention found that the rate of drug release can be controlled by utilizing the repulsive interaction between the base material and the contained hydrophilic drug.

Additionally, to the surprise of the inventors of the present invention, it was found that, when the condensation product is compounded as cationic monomer to a high compounding ratio, the polymer gel would not give rise to any degraded shape after the release of the drug contained and hence shows an excellent shape stability. The present invention is completed on the basis of these findings and achievements.

Thus, according to the present invention, there is provided an anionic drug-containing medical device comprising (1) an anionic drug; and (2) a copolymer which contains, as constituents, a cationic monomer including a condensation product of an alkyl quaternary ammonium compound having a substituted or unsubstituted aralkyl group and (meth) acrylic acid or a salt of the condensation product and a monomer capable of copolymerizing with the condensation product or the salt of the condensation product.

According to the present invention, preferably the condensation product of an alkyl quaternary ammonium compound having a substituted or unsubstituted aralkyl group and (meth)acrylic acid is expressed by general formula (I) shown below:

[chemical formula 1]

(wherein
$R_1$ represents a hydrogen atom or $CH_3$,
One or each of two or three of $R_2$ through $R_4$ independently represents a functional group expressed by general formula (II) shown below:

[chemical formula 2]

(wherein x represents an integer between 1 and 3 and each of $R_5$ through $R_9$ independently represents a hydrogen atom or a straight or branched chain hydrocarbon group having $C_1$ through $C_6$),
each of two, one or nil of the remaining ones of $R_2$ through $R_4$ represents a straight or branched chain hydrocarbon group having $C_1$ through $C_3$ and
n represents an integer between 1 and 4.

According to the present invention, preferably the copolymer of (2) as defined above further contains a hydrophilic monomer as a constituent, and the anionic drug-containing medical device as defined above is a hydrogel.

According to the present invention, preferably the compounding ratio of the cationic monomer as defined above is between 0.5 and 20 mol % relative to 1 mol of the hydrophilic monomer.

According to the present invention, preferably the anionic drug as defined above is either dexamethasone sodium phosphate or sodium cromoglicate.

Advantages of the Invention

An anionic drug-containing medical device according to the present invention, by employing a condensate of an alkyl quaternary ammonium compound having an aralkyl group and (meth)acrylic acid as a cationic monomer, the medical device can have no noticeable strength degradation of the gel base material even when the medical device is formed by using a cationic monomer at a high compounding ratio and made to contain an anionic drug at a high concentration level, and an excellent shape stability so that its shape is not degraded after the release of the anionic drug contained.

Therefore, it is expected that, by applying the anionic drug-containing medical device according to the present invention, eye disease treatment can be performed effectively, and the foreign-body sensation to wearers thereof and also the adverse effects that can be exerted to the optical properties of the device can be suppressed because the shape change between before and after the release of the anionic drug contained is minimal.

BEST MODE FOR CARRYING OUT THE INVENTION

Now, the present invention will be described in greater detail below.

An anionic drug-containing medical device according to the present invention comprises at least (1) an anionic drug and (2) a copolymer. The copolymer of (2) contains as constituents thereof at least a cationic monomer comprising a condensation product of an alkyl quaternary ammonium compound having a substituted or unsubstituted aralkyl group and (meth)acrylic acid or a salt of the condensation product and a monomer capable of copolymerizing with the condensation product or the salt of the condensation product.

An anionic drug-containing medical device according to the present invention is characterized in that a cationic monomer comprising a condensation product of an alkyl quaternary ammonium compound having a substituted or unsubstituted aralkyl group and (meth)acrylic acid is compounded therein as a component of the medical device that operates as a carrier of an anionic drug. Since a condensation product of an alkyl quaternary ammonium compound having a substituted or unsubstituted aralkyl group and (meth) acrylic acid provides a hydrophobic effect, the moisture holding ratio of the medical device would not remarkably increase even when it is compounded as a component for polymerization at a high compounding ratio. In other words, a medical device according to the present invention can suppress any undesirable fall of its strength and also any release of the drug it contains at a high concentration level in the initial stages of the use thereof because it can suppress any rise of its moisture holding ratio if it is made to contain the drug by a large amount due to the cationic monomer it contains at a high content ratio although the technological scope of the present invention is by no means limited by any conjectures. Additionally, the shape of a medical device according to the present invention is not degraded after releasing the drug it contains even when the condensation product is compounded to a high compounding ratio as cationic monomer. Furthermore, even if an anionic drug-containing medical device according to the present invention releases the drug it contains at a high concentration level, it does not show any significant change in its shape after releasing the drug and hence it shows excellent shape stability.

The cationic monomer to be used for the purpose of the present invention comprises at least a condensation product of an alkyl quaternary ammonium compound having a substituted or unsubstituted aralkyl group and (meth)acrylic acid or a salt thereof. The condensation product of an alkyl quaternary ammonium compound having a substituted or unsubstituted aralkyl group and (meth)acrylic acid is not subjected to any particular limitations so long as one of the alkyl groups of the quaternary ammonium compound comprising a substituted or unsubstituted aralkyl group and alkyl groups and the carboxyl group of the (meth)acrylic acid form an apparently condensed structure.

There are no particular limitations to the method to be used for preparing a condensation product of an alkyl quaternary ammonium compound having a substituted or unsubstituted aralkyl group and (meth)acrylic acid. In other words, it is not necessarily a method of literally preparing a condensation product of an alkyl quaternary ammonium compound having a substituted or unsubstituted aralkyl group and (meth)acrylic acid but may be a method of producing a substance having a structure apparently formed by condensing an alkyl quaternary ammonium compound having a substituted or unsubstituted aralkyl group and (meth)acrylic acid as a net result. For example, methacryloxyethyl dimethylbenzyl ammonium chloride, which is a specific example of a salt of a condensation product of an alkyl quaternary ammonium compound having a substituted or unsubstituted aralkyl group and (meth)acrylic acid, is available from MRC UNITEC and can be prepared by referring to Japanese Patent Application Laid-Open Publication No. 2001-106732 (which is incorporated by reference herein in its entirety).

For the purpose of the present invention, the cationic monomer as defined above may be a mixture of a condensation product of an alkyl quaternary ammonium compound having a substituted or unsubstituted aralkyl group and (meth)acrylic acid or a salt thereof and a monomer having a different cationic group.

In a specific mode, for example, the condensation product of an alkyl quaternary ammonium compound having a substituted or unsubstituted aralkyl group and (meth)acrylic acid may be a compound having a structure expressed by general formula (I) shown below:

[chemical formula 3]

(wherein
$R_1$ represents a hydrogen atom or $CH_3$,
One or each of two or three of $R_2$ through $R_4$ independently represents a functional group expressed by general formula (II) shown below:

[chemical formula 4]

(wherein x represents an integer between 1 and 3 and each of $R_5$ through $R_9$ independently represents a hydrogen atom or a straight or branched chain hydrocarbon group having $C_1$ through $C_6$), each of two, one or nil of the remaining ones of $R_2$ through $R_4$ represents a straight or branched chain hydrocarbon group having $C_1$ through $C_3$ and n represents an integer between 1 and 4.

Among the compounds that are expressed by the general formula (I), those that can suitably be used for the purpose of the present invention are, for example, such ones wherein $R_1$ is a hydrogen atom or $CH_3$ and one of $R_2$ through $R_4$ is a benzyl group, while each of the remaining two is $CH_3$ or $C_2H_5$ and n is an integer that is either 1 or 2. Among such compounds, methacryloxyethyl dimethylbenzyl ammonium chloride is a preferable one.

The compounding ratio of the cationic monomer is not subjected to any particular limitations so long as the device can maintain the given shape. For example, the compounding ratio may be between several mol % and tens of several mol % relative to the compounding ratio of the hydrophilic monomer, which is the second polymerization component as will be described hereinafter. As a specific example of the compounding ratio of the cationic monomer, it is preferably within a range not exceeding 30 mol % relative to a mol of the hydrophilic monomer, more preferably within a range between 0.5 and 20 mol % (between 0.005 and 0.2 mols), more preferably within a range between 0.5 and 10 mol % (between 0.005 and 0.1 mols). When the compounding ratio of the cationic monomer is less than 0.5 mol %, the quantity of the anionic drug that a medical device according to the present invention can contain is reduced. Then, it may be difficult to form an anionic drug-containing medical device that can provide a satisfactory therapeutic effect. When, on the other hand, the compounding ratio of the cationic monomer exceeds 30 mol %, the moisture holding ratio of the obtained medical device is high to make its shape unstable and, furthermore, the medical device cannot maintain a satisfactory level of strength and will give an uncomfortable wearing sensation to the user when it is actually worn by the user.

An anionic drug-containing medical device according to the present invention can be formed as hydrogel when a hydrophilic monomer is compounded as the second polymerization component in addition to the cationic monomer. The hydrophilic monomer to be used for the purpose of the present invention is not subjected to any particular limitations so long as it has at least a hydrophilic group and a (meth)acryloyl group or a vinyl group in the molecule and can feasibly be used for polymerization. Examples of hydrophilic monomers that can be used for the purpose of the present invention include hydroxymethyl (meth)acrylate, 2-hydroxyethyl (meth)acrylate, 2-hydroxypropyl (meth)acrylate, 2,3-dihydroxypropyl (meth)acrylate, 2-polyethyleneglycol mono(meth)acrylate, 2-polypropyleneglycol (meth)acrylate, N,N-dimethyl (meth)acrylamide, N,N-diethyl (meth)acrylamide and N-vinyl pyrrolidone. For the purpose of the present invention, anyone of such hydrophilic monomers may be used alone or two or more of such hydrophilic monomers may be used in combination.

While the compounding ratio of the hydrophilic monomer is not subjected to any particular limitations so long as the polymer produced by copolymerization with the hydrophilic monomer can take the form of hydrogel, it is typically between 50 and 90 wt %, preferably between 60 and 80 wt %, of all the polymerization components. When the compounding ratio of the hydrophilic monomer is less than 50 wt %, the softness of the obtained medical device will be low to consequently give an uncomfortable wearing sensation. When, on the other hand, the compounding ratio of the hydrophilic monomer exceeds 90 wt %, the cationic monomer may not be compounded by a sufficient amount.

A hydrophobic monomer may be compounded in an anionic drug-containing medical device according to the present invention as a polymerization component in order to control the outflow rate of the anionic drug into the tear in the device wearing eye of the user. Any hydrophobic monomer may be used for the purpose of the present invention provided that it does not have any hydrophilic group but has one or more (meth)acryloyl group or a vinyl group in the molecule and can feasibly be used for polymerization. Examples of hydrophobic monomers that can be used for the purpose of the present invention include (meth)acryl-based monomers such as trifluoroethyl methacrylate, methacryl amide, syloxanyl methacrylate, methyl methacrylate, n-butyl methacrylate, tert-butyl methacrylate, benzyl methacrylate, ethylhexyl methacrylate and lauryl (meth)acrylate; and silicone-containing monomers such as α-mono(methacryloyloxymethyl)polydimethyl siloxane, α,ω-di(methacryloxymethyl)polydimethyl siloxane, α-mono(3-methacryloyloxypropyl)polydimethyl siloxane, α,ω-di(3-methacryloyloxypropyl)polydimethyl siloxane, α-mono(3-methacryloyloxybutyl)polydimethyl siloxane, α,ω-di(3-methacryloyloxybutyl)polydimethyl siloxane, α-monovinylpolydimethyl siloxane, α,ω-divinylpolydimethyl siloxane, 3-tris(trimethylsiloxy)silylmethyl (meth)acrylate, 3-tris(trimethylsiloxy)silylpropyl (meth)acrylate, 3-methylbis(trimethylsiloxy)silylmethyl (meth)acrylate, 3-methylbis(trimethylsiloxy)silylpropyl (meth)acrylate, 3-trimethylsiloxydimethylsilylmethyl (meth)acrylate, 3-trimethylsiloxydimethylsilylpropyl (meth)acrylate and 3-methyldimethoxysilylpropyl (meth)acrylate. For the purpose of the present invention, any one of such hydrophobic monomers may be used alone or two or more of such hydrophobic monomers may be used in combination.

While the compounding ratio of the hydrophobic monomer in a medical device according to the present invention is not subjected to any particular limitations, it is typically between 0 and 30 wt %, preferably between 0 and 20 wt %, relative to the total weight of all the polarization components. When the compounding ratio of the hydrophobic monomer exceeds 30 wt %, the softness of the obtained medical device will be low to consequently give an uncomfortable wearing sensation and hence such a compounding ratio is not desirable.

A cross linking monomer may be compounded in addition to the above described components of a medical device according to the present invention for the purpose of forming a mesh structure in the polymer gel and adjusting the mechanical strength of the polymer gel. There are no particular limitations to the cross linking monomer to be used for this purpose so long as it is a compound having two or more (meth)acryl groups or vinyl groups in the molecule. Examples of cross linking monomers that can be used for the purpose of the present invention include ethyleneglycol di(meth)acrylate, methylene bis(meth)acrylamide, 2-hydroxy-1,3-di(meth)acryloxypropane and trimethylolpropane tri(meth)acrylate. Any one of such cross linking monomers may be used alone or two or more of such cross linking monomers may be combined for use.

While the compounding ratio of the cross linking monomer is not subjected to any particular limitations, it is typically between 0.3 and 10 mol %, preferably between 0.7 and 3 mol %, relative to the total number of moles of the polymerization components. When the compounding ratio of the cross linking monomer exceeds 10 mol %, the softness of the obtained anionic drug-containing medical device will be low to consequently give an uncomfortable wearing sensation and hence such a compounding ratio is not desirable.

A medical device according to the present invention can be manufactured by combining a number of manufacturing steps that are well known to those who are skilled in the art. While the method of manufacturing a medical device according to the present invention is not subjected to any particular limitations, it may typically include the following steps: preparing a monomer mixture solution by adding a polymerization initiator to the mixture of component monomers of an anionic drug-containing medical device and agitating and dissolving it; putting the obtained monomer mixture solution into a mold of a desired shape and obtaining a copolymer by means of a copolymerization reaction; obtaining a hydrogel by cooling the copolymer, releasing it from the mold, executing, if necessary, an operation of cutting and polishing, and subsequently causing the molded copolymer to be hydrated and swollen; and immersing the obtained hydro gel in a solution containing a dissolved drug to obtain an anionic drug-containing medical device holding the drug in the inside of the hydrogel.

Polymerization initiators that can be used for the purpose of the present invention include popular radical polymerization initiators, which include peroxide-based polymerization initiators such as lauroyl peroxide, cumene hydro peroxide and benzoyl peroxide; and azo-based polymerization initiators such as azo bis dimethylvarelonitrile and azo bis isobutylonitrile. Any one of such polymerization initiators may be employed alone or two or more of them may be combined for use. The ratio at which the polymerization initiator is added is not subjected to any particular limitations so long as it is sufficient for accelerating the copolymerization of the monomers, although preferably it may typically be between 10 and 7,000 ppm relative to the total weight of the monomers that are the polymerization components.

The step of obtaining a copolymer can successfully be executed by putting the monomer mixture solution in a mold typically made of metal, glass or plastic, hermetically sealing the mold, raising the temperature of the solution stepwise or continuously in a thermostatic bath or the like to between 25 and 120° C. and completing the polymerization in 5 to 120 hours. Ultraviolet rays, electron rays, gamma rays or the like may be used for polymerization. The solution polymerization can suitably be executed by adding water or an organic solvent to the monomer mixture solution.

In the step of obtaining a hydrogel, a hydrogel can be obtained after the end of the polymerization by cooling the molded polymer to room temperature, releasing the polymer from the mold and causing the polymer to be hydrated and swollen, if necessary, after executing a cutting and/or polishing operation. A liquid for causing the polymer to be swollen (polymer swelling solution) may typically be selected from water, saline, isotonic buffer solution and so on. The polymer swelling solution will be heated to between 60 and 100° C. and the polymer is immersed in the polymer swelling solution for a predetermined time period until it gets to a swollen state. Preferably, the monomers that are still contained in the polymer in an unpolymerized state are removed from the polymer during the swelling process.

The step of obtaining an anionic drug-containing medical device is executed by immersing the hydrogel obtained by way of the above described steps into a solution containing an anionic drug in a dissolved state and executing a steam sterilization process at high temperature under high pressure. The anionic drug will be held in the hydrogel by ionic bonding between the drug and the cationic group provided by the cationic monomer, which is a component of the hydrogel. Since this step is executed at high temperature under high pressure, it also takes the role of an autoclave sterilization process. Then, as a result, the user can wear the anionic drug-containing medical device safely and soundly and the medical device can be produced without requiring an additional sterilization step.

The anionic drug to be used for the purpose of the present invention is not subjected to any particular limitations so long as it is a drug having an anionic group such as a sulfo group, a carboxyl group or a phosphoric acid group. Preferable examples of drugs having a sulfo group include azulene sodium sulfonate, dexamethasone metasulfobenzoate sodium and chondroitin sulfate sodium. Preferable examples of drugs having a carboxyl group include sodium cromoglicate, potassium cromoglicate, bromfenac sodium, diclofenac sodium, valsartan, dexamethasone sodium phosphate, betamethasone sodium phosphate, moxifloxacin, amlexanox, pranoprofen, norfloxacin, ofroxacin, sodium hyaluronate and chondroitin sulfate sodium. Preferable examples of drugs having a phosphoric acid group include dexamethasone sodium phosphate and betamethasone sodium phosphate. For the purpose of the present invention, any one of such anionic drugs may be used alone or two or more of such anionic drugs may be used in combination.

There are no particular limitations to the solvent to be used for dissolving a drug for the purpose of the present invention. Examples of solvents that can be used include water, hydrophilic solvents and a mixture solvent of water and a hydrophilic solvent. While the hydrophilic solvent to be used for the purpose of the present invention is not subjected to any particular limitations, preferable examples of hydrophilic solvents include alcohols such as ethanol, methanol, isopropanol and n-butanol, dimethyl sulfoxide and buffer solutions.

The concentration of the drug contained in the drug solution is not subjected to any particular limitations. In other words, the concentration of the drug can be selected appropriately by considering the solubility of the drug, the lowest effective concentration of the drug necessary for expressing the therapeutic effect thereof, the highest safe concentration and so on of the drug.

An anionic drug-containing medical device according to the present invention can find various applications by manipulating the shape thereof. More specifically, it can be used as ophthalmic lens such as contact lens by making it show a given radius of curvature. The drug can effectively be delivered from the sclera surface to the tissue of the posterior segment tissue of an eye by making it show a ring-like profile that snugly covers the sclera of the eye. Alternatively, it can be utilized as a cover for a wound or as a poultice when it is made to show a sheet-like profile.

Now, the present invention will be described in greater detail by way of examples. Note, however, that the present invention is by no means limited by those examples and can be realized in various different modes so long as such modes can effectively dissolve the problem to be solved by the present invention.

Examples

Preparation of Drug-Containing Medical Devices in Examples (1) Through (8)

In each of these examples, to a mixture containing 2-hydroxyethylmethacrylate (HEMA) and methacryloxyethyl dimethylbenzyl ammonium chloride (MOEBAC), the content ratio relative to 1 mol of HEMA being listed in Table 1, polyethyleneglycol diacrylate (A-200) and azo bis isobutylonitrile (AIBN) were added respectively by 1 mol % relative to the total number of moles of the monomers and by 3,000 ppm (external) relative to the total weight of the monomers and then they were mixed and agitated to obtain a monomer mixture solution. The obtained monomer mixture solution was poured into a mold and the temperature of the mixture solution was raised to a range between 30 and 110° C. in 17 hours to cause a copolymerization reaction to take place in order to obtain an intended polymer. The obtained polymer was cooled to room temperature and released from the mold. Thereafter, the polymer was immersed sequentially into a 60° C. warm phosphoric acid buffer solution containing ethanol for 1 hour and into a phosphoric acid buffer solution also for 1 hour and then immersed into pure water at room temperature for over 2 hours to obtain a hydrated and swollen hydrogel. In each of Examples (1) through (4), (7) and (8), the obtained hydrogel was immersed into a 0.2 wt % aqueous solution of dexamethasone sodium phosphate (DSP) and, in each of Examples (5) and (6), the obtained hydrogel was immersed into a 1.0 wt % aqueous solution of sodium cromoglicate (DSCG). Thereafter, the hydrogels were steam-sterilized at 121° C. under high pressure for 30 minutes to obtain the stylized devices of Examples (1) through (8).

Preparation of Drug-Containing Medical Devices in Comparative Examples (1) Through (8)

In each of Comparative Examples (1) through (8), a hydrated and swollen hydrogel was prepared as in Examples (1) through (8) except that methacryl amide propyl trimethyl ammonium chloride (MAPTAC) was used at the ratio as listed in Table 1 instead of MOEBAC. In each of Comparative Examples (1) through (4) and (7), the obtained hydrogel was immersed in a 0.2 wt % aqueous solution of DSP and, in each of Comparative Examples (5) and (6), the obtained hydrogel was immersed in a 1.0 wt % aqueous solution of DSCG. Thereafter, the hydrogels were steam-sterilized at 121° C. under high pressure for 30 minutes to obtain the stylized devices of Comparative Examples (1) through (7). No stylized device was formed in Comparative Example (8).

Evaluation Method for Medical Devices Adapted to Sustained Release of Anionic Drug (1) Measurement of Moisture Holding Ratio After the containing the anionic drug, the stylized device in each of Examples (1) through (8) and Comparative Examples (1) through (7) was taken out from the drug solution and the excess moisture was wiped out. Subsequently, the weight ($W_1$) of the moisture-containing device was measured. Thereafter, the device was dried by means of a dryer at $60^2$C for 24 hours and then the weight ($W_2$) of the device was measured again. The moisture holding ratio of the device was determined by using the mathematical formula shown below.

$$\text{moisture holding ratio (wt \%)} = [(W_1 - W_2)/W_1] \times 100$$

(2) Measurement of Contained Amount of Anionic Drug

After containing the anionic drug, the stylized device in each of Examples (1) through (8) and Comparative Examples (1) through (7) was immersed in saline and remained left at room temperature for 72 hours in order to cause the device to gradually release the drug contained in the inside thereof into saline. After the sustained release of the anionic drug, the anionic drug in saline was quantified by means of high performance liquid chromatography (HPLC, available from JASCO Corporation) in accordance with a generally accepted method. The obtained value was used as the anionic drug content rate (μg/g) of the device.

(3) Tensile Strength

Each of the test pieces was adjusted according to the Standard Test Method for Tensile Properties of Plastics (JIS K7113) and each of the stylized devices of Examples (1) through (8) and Comparative Examples (1) through (7) that had taken in the drug and swollen was tested for tensile strength.

○: not less than 1.5 MPa
x: less than 1.5 MPa (4) Shape Stability

After the sustained release of the drug, the shape of each of the stylized devices of Examples (1) through (8) and Comparative Examples (1) through (7) was visually checked by means of a dimension analyzer.

○: true circle without any irregularity on the surface
x: not true circle and/or irregularity on the surface

TABLE 1

|  |  | (1) | (2) | (3) | (4) | (5) | (6) | (7) | (8) |
|---|---|---|---|---|---|---|---|---|---|
| Example | MOEBAC (mol %) | 0.5 | 1 | 1.25 | 2.5 | 5 | 10 | 15 | 20 |
|  | moisture holding ratio (%) | 37.2 | 37.1 | 37.4 | 37.9 | 37.7 | 38.0 | 41.1 | 44.6 |
|  | drug | DSP | DSP | DSP | DSP | DSCG | DSCG | DSP | DSP |
|  | drug content rate (μg/g) | 3039 | 4769 | 5258 | 10753 | 31534 | 44120 | 47200 | 64322 |
|  | strength (MPa) | 2.34 | 2.29 | 2.26 | 2.12 | 2.01 | 1.72 | 1.64 | 1.56 |
|  |  | ○ | ○ | ○ | ○ | ○ | ○ | ○ | ○ |
|  | Stability | ○ | ○ | ○ | ○ | ○ | ○ | ○ | ○ |
| Comp. Example | MOEBAC (mol %) | — | — | — | — | — | — | — | — |
|  | MAPTAC (mol %) | 0.5 | 1 | 1.25 | 2.5 | 5 | 10 | 15 | 20 |
|  | moisture holding ratio (%) | 38.8 | 40.5 | 41.1 | 42.6 | 45.5 | 52.7 | 59.4 | unformable |
|  | drug | DSP | DSP | DSP | DSP | DSCG | DSCG | DSP | — |

TABLE 1-continued

|  | (1) | (2) | (3) | (4) | (5) | (6) | (7) | (8) |
|---|---|---|---|---|---|---|---|---|
| drug content rate (µg/g) | 2508 | 3328 | 3974 | 5445 | 21558 | 36323 | 40120 | — |
| strength (MPa) | 2.33 | 2.18 | 2.11 | 1.70 | 1.43 | 1.06 | 0.76 | — |
|  | ○ | ○ | ○ | ○ | x | x | x | — |
| Stability | ○ | ○ | ○ | ○ | ○ | ○ | x | — |

What the abbreviations in Table 1 stand for are described below.
HEMA: 2-hydroxyethyl methacrylate
MOEBAC: methacryloxyethyl dimethylbenzyl ammonium chloride
MAPTAC: methacryl amide propyl trimethyl ammonium chloride
A-200: polyethyleneglycol diacrylate
AIBN: azo bis isobutylonitrile
DSP: dexamethasone sodium phosphate
DSCG: sodium cromoglicate In each of Examples (1) through (8), if the compounding ratio of the cationic monomer was raised to between 0.5 and 20 mol %, the resultant rise of the moisture holding ratio was as small as 19.9% as a whole. Therefore, the strength of the device was maintained (decrease ratio: 33.3%) and the shape did not show any change after the release of the anionic drug.

On the other hand, in each of Comparative Examples (1) through (7), where the cationic monomer was compounded at a ratio same as that of each of Examples, the increase ratio of the moisture holding ratio was as large as 53.1%, which is much higher than those of Examples, because the cationic monomer used for it had no benzene ring in the molecule. Thus, the device showed a remarkable fall of the strength (decrease ratio: 67.4%) and the shape stability tended to be degraded after the release of the anionic drug contained.

Figure 1:
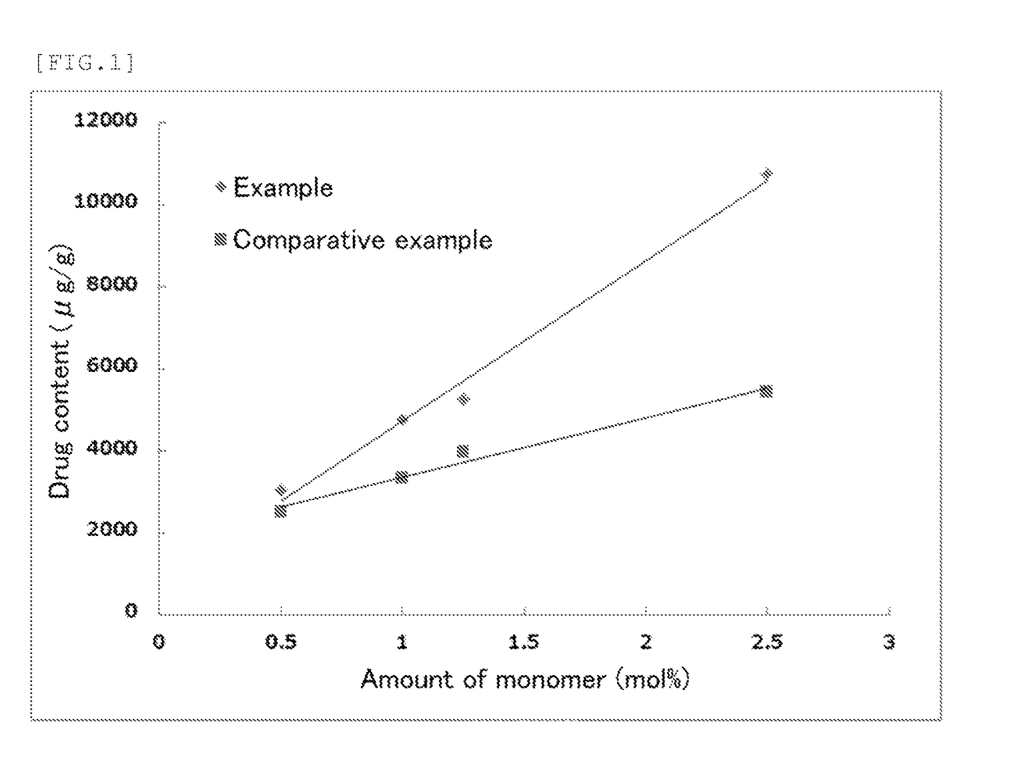
FIG. 1 is a graph illustrating the relationship between the content of the cationic monomer and the drug containing ratio of each of Examples 1 through 4 and Comparative Examples 1 through 4.

Furthermore, when the devices of Examples and Comparative Examples were made to contain a cationic monomer at the same mole ratio, the devices of Examples, wherein a cationic monomer having a benzene ring in the molecule was employed, took in the anionic drug to a higher ratio if compared with the devices of Comparative Examples, wherein a cationic monomer having no benzene ring in the molecule was used. This fact is also clearly seen from FIG. 1 showing a graph illustrating the relationship between the content of the cationic monomer and the amount of drug contained in each of the devices of Examples (1) through (4) and Comparative Examples (1) through (4), both of which showed a certain level of strength. As seen from FIG. 1, the devices of Examples showed a large increase in drug intake quantity due to the contents of the monomers used for them if compared with those of Comparative examples.

Figure 2:
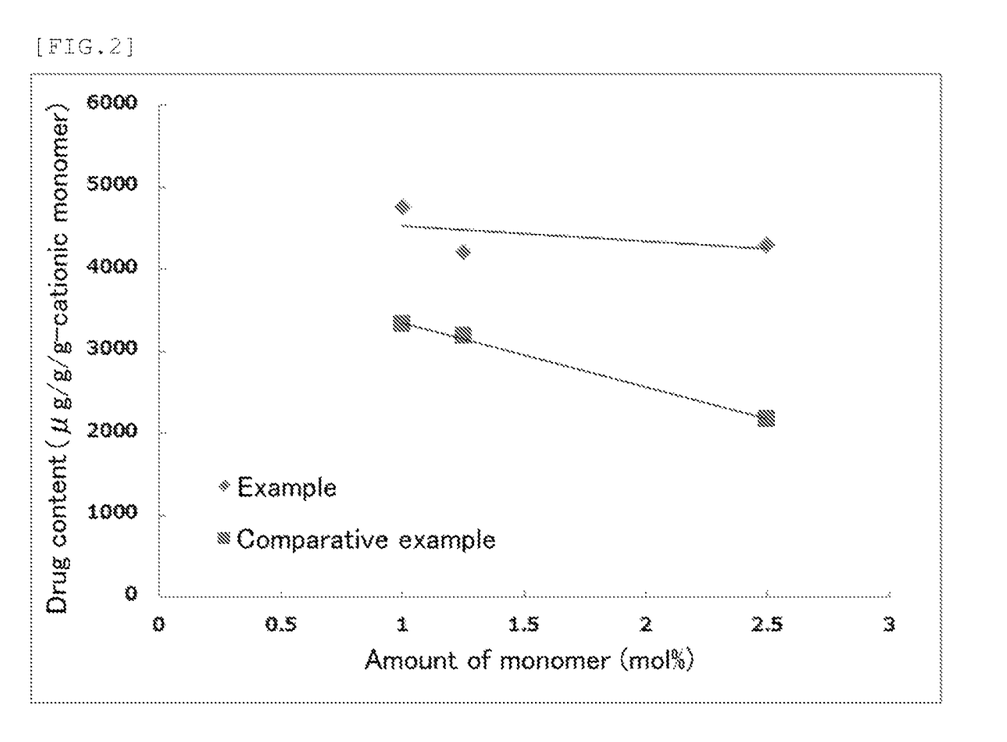
FIG. 2 is a graph illustration the relationship between the content of the cationic monomer and the drug containing ratio per unit of the cationic monomer in each of Examples 1 through 3 and Comparative Examples 1 through 3.

FIG. 2 shows a graph illustrating the relationship between the content of the cationic monomer and the quantity of drug intake per unit of the cationic monomer in each of the sample devices of Examples (1) through (3) and Comparative Examples (1) through (3). As seen from FIG. 2, it is clear that the quantity of drug intake per unit of the cationic monomer is less influenced by the content of the cationic monomer in the devices of Examples (1) through (3), compared with Comparative Examples (1) through (3). Therefore, it was proved that the quantity of drug intake can reliably be increased in each of Examples by raising the content of the cationic monomer the device contains if compared with Comparative Examples so that a medical device showing a desired level of drug intake can be designed and manufactured much easier by using the technique of Examples if compared with Comparative Examples.

As described above, by using a cationic monomer having a benzene ring in the molecule thereof as a component of the drug carrier, the present invention can provide a medical device that shows both a high shape stability after the release of the drug contained and a remarkable therapeutic effect because the quantity of the drug the device contains can be increased without giving rise to an increased moisture holding ratio and a strength degradation.

INDUSTRIAL APPLICABILITY

A medical device according to the present invention can be made to intake a desired quantity of drug in a controlled manner and shows excellent gel strength and remarkable shape stability after the release of the drug contained so that it is highly safe to the wearer of the device and can provide an excellent therapeutic effect. It can contribute to human health and welfare.

The invention claimed is:
1. An anionic drug-containing contact lens comprising:
(1) an anionic drug; and
(2) a copolymer which consists of, as constituent, at least one cationic monomer consisting of methacryloxyethyl dimethylbenzyl ammonium chloride, at least one hydrophilic monomer, at least one cross-linking monomer, and optionally at least one hydrophobic monomer,
wherein the compounding ratio of the cationic monomer is between 2.5 and 15 mol % relative to 1 mol of the hydrophilic monomer,
wherein the anionic drug-containing contact lens is a hydrogel,
wherein the at least one hydrophilic monomer is one or more selected from the group consisting of hydroxymethyl (meth)acrylate, 2-hydroxyethyl (meth)acrylate, 2-hydroxypropyl (meth)acrylate, 2,3-dihydroxypropyl (meth)acrylate, 2-polyethyleneglycol mono(meth)acrylate, 2-polypropyleneglycol (meth)acrylate, N,N-dimethyl (meth)acrylamide, N,N-diethyl (meth)acrylamide and N-vinylpyrrolidone.
2. The anionic drug-containing contact lens of claim 1, wherein the anionic drug is either dexamethasone sodium phosphate or sodium cromoglicate.
3. The anionic drug-containing contact lens of claim 1, where the anionic drug-containing contact lens was subjected to autoclave sterilization.

4. The anionic drug-containing contact lens of claim 1, where the anionic drug-containing contact lens was subjected to steam sterilization.

\* \* \* \* \*